(12) United States Patent
Jung et al.

(10) Patent No.: US 10,362,964 B2
(45) Date of Patent: Jul. 30, 2019

(54) METHOD, APPARATUS, AND SYSTEM FOR PROVIDING MEDICAL IMAGE

(71) Applicant: SAMSUNG ELECTRONICS CO., LTD., Suwon-si (KR)

(72) Inventors: Yun-sub Jung, Yongin-si (KR); Hwan Shim, Yongin-si (KR); Seoung-hun Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1036 days.

(21) Appl. No.: 14/696,882

(22) Filed: Apr. 27, 2015

(65) Prior Publication Data

US 2015/0320324 A1   Nov. 12, 2015

(30) Foreign Application Priority Data

May 9, 2014   (KR) ........................ 10-2014-0055750

(51) Int. Cl.
*A61B 5/00*   (2006.01)
*A61B 5/06*   (2006.01)
(Continued)

(52) U.S. Cl.
CPC .......... *A61B 5/066* (2013.01); *A61B 5/02007* (2013.01); *A61B 5/6852* (2013.01); *A61B 5/748* (2013.01); *G06T 7/62* (2017.01); *A61B 2034/2065* (2016.02); *A61B 2090/364* (2016.02); *A61B 2090/376* (2016.02); *A61B 2560/0475* (2013.01); *A61B 2576/02* (2013.01);
(Continued)

(58) Field of Classification Search
CPC ..... A61B 5/066; A61B 5/02007; A61B 5/748; A61B 5/6852; A61B 2090/364; A61B 2090/376; A61B 2034/2065; A61B 2576/02; A61B 2560/0475; G06T 7/62; G06T 2207/10081; G06T 2207/30101; G06T 2207/10088
See application file for complete search history.

(56) References Cited

U.S. PATENT DOCUMENTS 6,546,271 B1   4/2003   Reisfeld
7,684,850 B2   3/2010   Govari et al.
(Continued)

FOREIGN PATENT DOCUMENTS

KR   10-2001-0067270 A   7/2001
KR   10-2006-0081367 A   7/2006
(Continued)

*Primary Examiner* — Joel Lamprecht
(74) *Attorney, Agent, or Firm* — Sughrue Mion, PLLC

(57) ABSTRACT

A method of providing a medical image by using a medical imaging apparatus includes: acquiring blood vessel information indicating information about a blood vessel, the blood vessel being included in a medical image; and displaying the medical image. The blood vessel information includes at least one of a first diameter of the blood vessel, a first angle of the blood vessel, and a presence of at least one of bifurcation and crossover, in a first region of interest (ROI) with respect to a first position in the medical image. The acquiring of the blood vessel information includes acquiring blood vessel information corresponding to a second ROI with respect to a second position, based on the blood vessel information corresponding to the first ROI.

18 Claims, 11 Drawing Sheets

(51) Int. Cl.
 *A61B 5/02* (2006.01)
 *G06T 7/62* (2017.01)
 A61B 90/00 (2016.01)
 A61B 34/20 (2016.01)
(52) U.S. Cl.
 CPC ............... *G06T 2207/10081* (2013.01); *G06T 2207/10088* (2013.01); *G06T 2207/30101* (2013.01)

(56) References Cited

U.S. PATENT DOCUMENTS

| | | |
|---|---|---|
| 2004/0097805 A1 | 5/2004 | Verard et al. |
| 2005/0080328 A1 | 4/2005 | Vass et al. |
| 2007/0276216 A1 | 11/2007 | Beyar et al. |
| 2008/0221435 A1 | 9/2008 | Rasche |
| 2008/0294034 A1 | 11/2008 | Krueger et al. |
| 2009/0306497 A1 | 12/2009 | Manzke et al. |
| 2010/0172556 A1* | 7/2010 | Cohen ..................... A61B 6/12 382/128 |
| 2014/0270436 A1* | 9/2014 | Dascal ..................... G06T 7/11 382/130 |

FOREIGN PATENT DOCUMENTS

| | | |
|---|---|---|
| KR | 10-2010-0074377 A | 7/2010 |
| KR | 10-1306332 B1 | 9/2013 |

\* cited by examiner

METHOD, APPARATUS, AND SYSTEM FOR PROVIDING MEDICAL IMAGE

CROSS-REFERENCE TO RELATED APPLICATION

This application claims priority from Korean Patent Application No. 10-2014-0055750, filed on May 9, 2014, in the Korean Intellectual Property Office, the disclosure of which is incorporated herein in its entirety by reference.

BACKGROUND

1. Field

Apparatuses, methods, and systems consistent with exemplary embodiments relate to providing a medical image, and more particularly, to detecting and providing information about a blood vessel included in a medical image.

2. Description of the Related Art

A blood vessel intervention is used for the treatment of various diseases associated with a blood vessel, in addition to cerebrovascular or cardiovascular treatment. The blood vessel intervention is a medical procedure in which a small hole is formed in the skin, a catheter or a medical induction wire is directly inserted into a blood vessel, and treatment is performed while observing the inside of a human body by using a medical imaging apparatus. Blood vessel intervention is performed using only a minimum incision. In the blood vessel intervention, an operator may observe a blood vessel of a human body in real time, and a blood vessel angiography may be used to observe a blood vessel in a non-invasive manner.

The blood vessel angiography for observing a blood vessel includes various methods. For example, the blood vessel angiography may include a method using a magnetic resonance angiography (MRA) image, a method using a computed tomography angiography (CTA) image, a method using an ultrasound image, and a method using an X-ray image. In the method using the MRA image or the CTA image, a time taken to acquire an image is relatively long. Therefore, the MRA image or the CTA image is mainly used for planning before a medical procedure or observing a state of a patient after a medical procedure. An X-ray fluoroscopy for observing a blood vessel in real time may be used while the blood vessel intervention is being performed. The X-ray fluoroscopy is a method in which a contrast agent is injected into a blood vessel of a human body, and an X-ray image of the blood vessel is acquired.

In the blood vessel intervention, an operator may move a catheter inserted into a blood vessel while viewing a two-dimensional (2D) medical image. A time taken to move a catheter to a lesion may be changed depending on a skill level of an operator. When a time taken to move a catheter increases, a procedure time increases. As a procedure time increases, a time during which a patient is exposed to radiation increases. On the other hand, when moving a catheter at an excessively high speed, a wall of a blood vessel may be damaged by the catheter.

SUMMARY

One or more exemplary embodiments include a method and an apparatus for acquiring blood vessel information from a medical image including a blood vessel.

One or more exemplary embodiments include a method and an apparatus, which more accurately display a position of a catheter, inserted into a human body, on a medical image.

One or more exemplary embodiments include a method and an apparatus, which provide a traveling path, through which a catheter is to be moved, to an operator by using blood vessel information.

One or more exemplary embodiments include a method and an apparatus, which more easily match a three-dimensional (3D) image with a two-dimensional (2D) image.

One or more exemplary embodiments include a method and an apparatus, which provide a feedback to a user depending on a position of a catheter.

According to an aspect of an exemplary embodiment, a medical image providing method, performed by a medical imaging apparatus, includes: acquiring blood vessel information about a blood vessel included in a medical image; and displaying the medical image, wherein the acquiring of the blood vessel information includes: a) determining a diameter and an angle of a blood vessel included in a first region of interest (ROI), and detecting bifurcation and crossover, in the first ROI which is set at a first position in the medical image; and b) tracking the blood vessel.

The tracking of the blood vessel may include: determining a second position, based on the first position, the determined angle, and the detected bifurcation; determining a diameter and an angle of a blood vessel included in a second ROI, and detecting bifurcation and crossover, in the second ROI which is set at a second position in the medical image.

The medical image providing method may further include: determining a start point and a target point in the medical image; and displaying a traveling path which is determined based on the start point, the target point, and the blood vessel information.

The displaying of the traveling path may include displaying a plurality of traveling paths according to number of bifurcations included in the blood vessel information.

The medical image providing method may further include: matching the medical image with a three-dimensional (3D) medical image; and determining a 3D traveling path corresponding to the traveling path, in the 3D medical image, wherein the displaying of the traveling path may include further displaying the 3D medical image including the 3D traveling path.

The medical image providing method may further include acquiring position information of a catheter by using a position sensor included in the catheter and two fixed position sensors, wherein the displaying of the medical image may include marking a position of the catheter on the medical image, based on the position information.

The medical image providing method may further include outputting feedback information, based on the position information of the catheter and the blood vessel information.

The medical image providing method may further include: acquiring traveling history information that is a history in which the position information of the catheter has moved; and reconstructing the medical image or the blood vessel information, based on the traveling history information.

The medical image providing method may further include: matching the medical image with a three-dimensional (3D) medical image by using the traveling history information; and marking a position of the catheter on the 3D medical image.

Step a) may include determining the angle of the blood vessel, based on the diameter of the blood vessel and a mean pixel value of the blood vessel.

According to an aspect of an exemplary embodiment, a medical imaging apparatus for providing a medical image includes: an image processor that acquires blood vessel information about a blood vessel included in a medical image; and a display that displays the medical image, wherein the image processor determines a diameter and an angle of a blood vessel included in a first region of interest (ROI), detects bifurcation and crossover, and tracks the blood vessel, in the first ROI which is set at a first position in the medical image.

The image processor may determine a second position, based on the first position, the determined angle, and the detected bifurcation, and determine a diameter and an angle of a blood vessel included in a second ROI and detect bifurcation and crossover, in the second ROI which is set at a second position in the medical image, thereby tracking the blood vessel.

The medical imaging apparatus may further include an input device that receives information from a user, wherein the image processor may determine a start point and a target point in the medical image, based on the information received through the input device, and determine a traveling path, based on the start point, the target point, and the blood vessel information, and the display may display the determined traveling path.

The display may display a plurality of traveling paths according to number of bifurcations included in the blood vessel information.

The image processor may match the medical image with a three-dimensional (3D) medical image, and determine a 3D traveling path corresponding to the traveling path, in the 3D medical image, and the display may display the 3D medical image including the 3D traveling path.

The medical imaging apparatus may further include a position information acquirer that acquires position information of a catheter by using a position sensor included in the catheter and two fixed position sensors, wherein the display may mark a position of the catheter on the medical image, based on the position information.

The medical imaging apparatus may further include a feedback output device that outputs feedback information, based on the position information of the catheter and the blood vessel information.

The image processor may acquire traveling history information that is a history in which the position information of the catheter has moved, and reconstruct the medical image or the blood vessel information, based on the traveling history information.

The image processor may match the medical image with a three-dimensional (3D) medical image by using the traveling history information, and the display may mark a position of the catheter on the 3D medical image.

The image processor may determine the angle of the blood vessel, based on the diameter of the blood vessel and a mean pixel value of the blood vessel.

According to an aspect of an exemplary embodiment, provided is a non-transitory computer-readable storage medium storing a program for executing the method.

According to an aspect of an exemplary embodiment, an apparatus for providing a medical image includes a controller configured to set a start point and a target point in a blood vessel of an object, and acquire a path from the start point to the target point through the blood vessel by using information about the blood vessel, the information being obtained by analyzing a medical image of the object; and a display configured to display the medical image including the path, wherein the information comprises at least one of a diameter and an angle of the blood vessel.

The controller may set a region of interest (ROI) in the medical image and acquire at least a portion of the path corresponding to the ROI.

In response to obtaining information about the blood vessel in a first ROI with respect to a first position, the controller may set a second ROI with respect to a second position, and a size of the second ROI may be determined by using the following equation: $ROI_{size}=\alpha \times (\Delta v/\Delta \theta)$, wherein $\alpha$ denotes a constant, $\Delta v$ denotes the diameter of the blood vessel in the first ROI, and $\Delta \theta$ denotes a difference between a first angle of the blood vessel, the first angle being determined in the first ROI, and a second angle of the blood vessel, the second angle being determined in an ROI that precedes the first ROI.

The controller may set the start point and the target point based on an input from a user.

The controller may set the start point based on a point at which a catheter is inserted in the blood vessel and set the target point based on a position of a lesion.

BRIEF DESCRIPTION OF THE DRAWINGS

The above and/or other aspects will become more apparent by describing certain exemplary embodiments with reference to the accompanying drawings.

DETAILED DESCRIPTION

Figure 1:
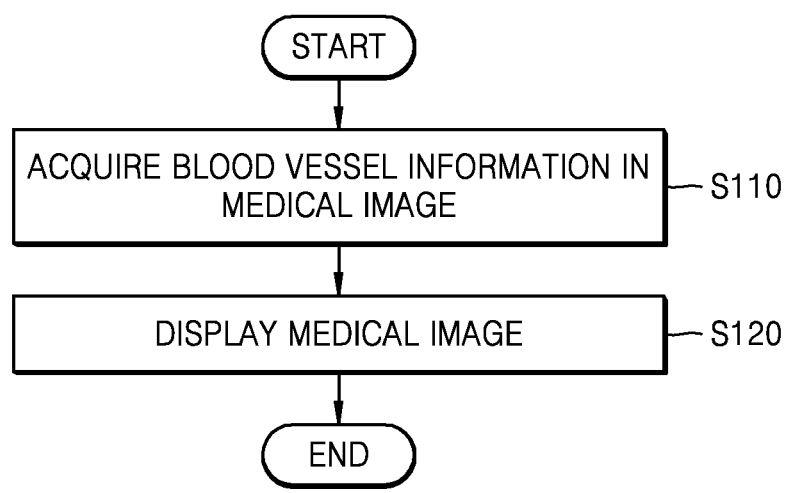
FIG. 1 is a flowchart illustrating a process of providing a medical image, according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

In this disclosure below, when one part (or element, device, etc.) is referred to as being 'connected' to another part (or element, device, etc.), it should be understood that the former may be 'directly connected' to the latter, or 'electrically connected' to the latter via an intervening part (or element, device, etc.). Furthermore, when it is described that one part comprises (or includes or has) some elements, it should be understood that the one part may comprise (or include or has) only those elements, or may comprise (or include or have) other elements as well as those elements if there is no specific limitation.

A medical image denotes an image that is obtained by capturing the inside of a human body with a medical imaging apparatus. For example, the medical image may be a blood vessel angiogram image which is obtained by capturing a blood vessel by using an X-ray fluoroscopy.

Blood vessel information denotes information about a blood vessel in a medical image. For example, the blood vessel information may include information about a diameter of a blood vessel, an angle of the blood vessel in a medical image with respect to a horizontal direction, and bifurcation and/or crossover included in the medical image.

Bifurcation denotes one blood vessel being divided into two or more blood vessels. Also, crossover denotes different blood vessels intersecting each other in a medical image.

A three-dimensional (3D) medical image denotes an image that is obtained by reconstructing images, acquired by capturing (or photographing) the inside of a human body, to a 3D image. For example, the 3D medical image may a 3D magnetic resonance (MR) image or a 3D computed tomography (CT) image, but is not limited thereto.

A start point denotes a position from which a traveling path (or a path of a catheter) starts in a medical image or an analysis of the medical image starts. For example, a position corresponding to a point in which a catheter is inserted into a human body in a medical image may be the start point. Also, a target point denotes a position that is a destination of a traveling path. For example, a position of a lesion in a medical image may be the target point. Also, a termination point denotes a point in which an analysis of blood vessel information terminates. For example, a point in which a diameter of a blood vessel is equal to or less than a threshold value may be the termination point.

FIG. 1 is a flowchart illustrating a process of providing a medical image, according to an exemplary embodiment.

In operation S110, a medical imaging apparatus may acquire blood vessel information from a medical image. The medical imaging apparatus may analyze a diameter and/or a position of a blood vessel in the medical image. Also, the medical imaging apparatus may analyze an angle of the blood vessel in the medical image with respect to a horizontal direction. Also, the medical imaging apparatus may determine whether a point in which blood vessels in the medical image meet each other corresponds to bifurcation or crossover.

Subsequently, in operation S120, the medical imaging apparatus may display the medical image from which the blood vessel information is acquired. Here, the medical imaging apparatus may display the blood vessel information which is acquired in operation S110. For example, the medical imaging apparatus may mark a diameter of a blood vessel on the medical image. That is, the medical imaging apparatus may display the acquired blood vessel information along with the medical image.

Figure 2:
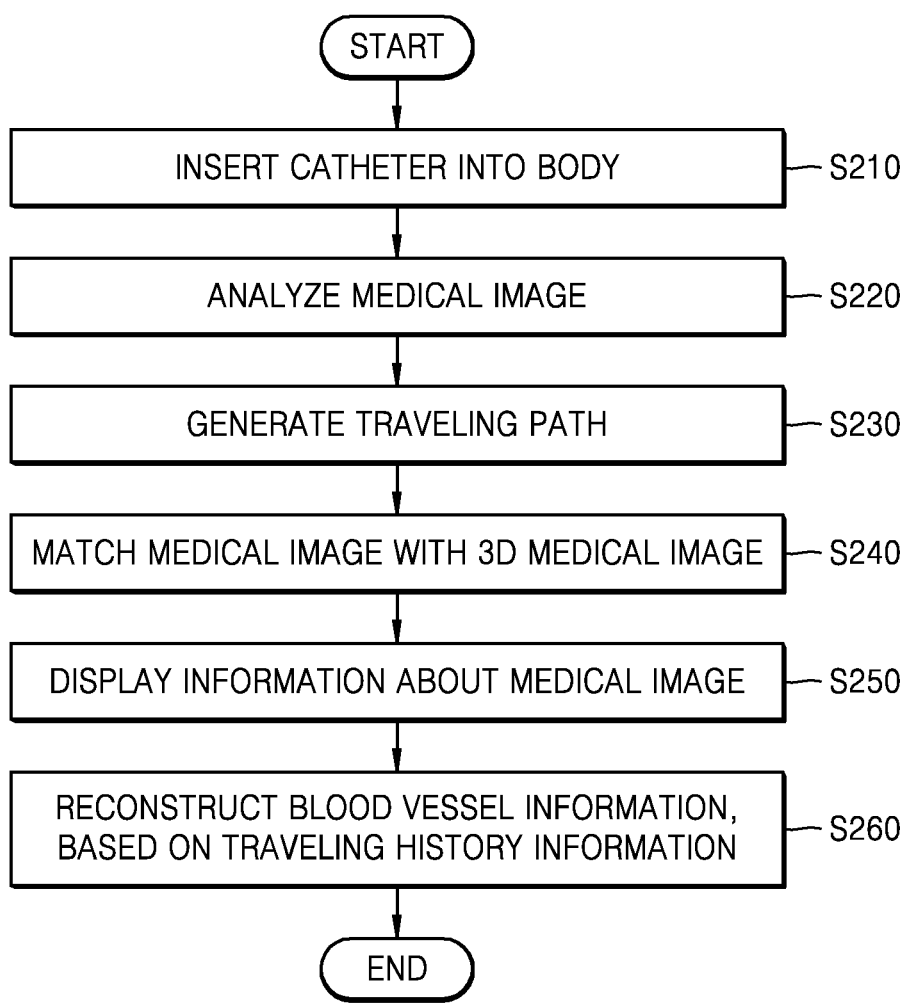
FIG. 2 is a flowchart illustrating a process of providing a medical image, according to an exemplary embodiment.

FIG. 2 is a flowchart illustrating a process of providing a medical image, according to another exemplary embodiment.

First, in operation S210, an operator may insert a catheter into a body of a patient, for performing a blood vessel intervention. In operation S220, a medical imaging apparatus may analyze a medical image, for acquiring blood vessel information which is used for the operator to perform the blood vessel intervention. Operation S220 will be described in detail with reference to FIGS. 3, 4, 5, 6, and 7.

Subsequently, in operation S230, the medical imaging apparatus may generate a traveling path (or a path of the catheter), based on the acquired blood vessel information. In operation S230, the medical imaging apparatus may determine a start point and a target point. Here, a user may set the start point and the target point by using the medical imaging apparatus. Alternatively, the medical imaging apparatus may detect a position in which the catheter is inserted in operation S210, and determine the position, in which the catheter is inserted, as the start point. Also, the medical imaging apparatus may detect a position of a lesion in the medical image and determine the position of the lesion as the target point. A method in which the medical imaging apparatus generates a traveling path will be described in detail with reference to FIGS. 8 and 9.

In operation S240, the medical imaging apparatus may match the medical image with a 3D medical image. According to an exemplary embodiment, the medical imaging apparatus may acquire position information of the catheter. An exemplary embodiment of acquiring position information of a catheter will be described in detail with reference to FIG. 11. The medical imaging apparatus may match the medical image with the 3D medical image by using the blood vessel information which is acquired in operation S220 and the position information of the catheter. Generally, matching a two-dimensional (2D) image with a 3D image may take a considerable amount of time. However, according to an exemplary embodiment, a position of a 2D image that corresponds to a 3D image is more easily determined by using a position of a blood vessel in a medical image and position information of a catheter. Therefore, the medical imaging apparatus according to an exemplary embodiment provides in real time a 3D image matched with a 2D medical image.

subsequently, in operation S250, the medical imaging apparatus may display the 2D or 3D medical image and information about the medical image. Here, the information about the medical image may include at least one of blood vessel information and a traveling path. For example, the medical imaging apparatus may display a diameter of a blood vessel or the traveling path.

Subsequently, in operation S260, the medical imaging apparatus may reconstruct (or update) the blood vessel information, based on traveling history information. The medical imaging apparatus may store a position to which the catheter has moved. The traveling history information denotes a path through which the catheter has actually moved in a body of a patient. That is, the catheter moves along the inside of the blood vessel. Therefore, when a position of the blood vessel detected from the medical image differs from a position of the blood vessel according to a movement of the catheter, the medical imaging apparatus may reconstruct the blood vessel information or the medical image, based on the traveling history information. That is, a blood vessel map may be reconstructed by using a moving path comprising 3D coordinates of the catheter.

Figure 3:
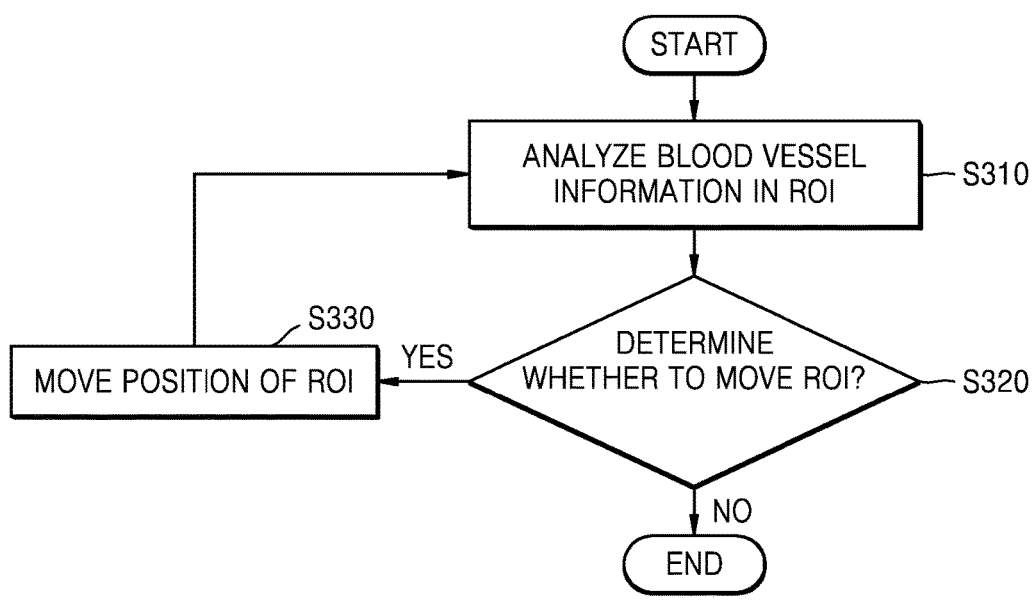
FIG. 3 is a flowchart illustrating a method of acquiring blood vessel information from a medical image, according to an exemplary embodiment.

FIG. 3 is a flowchart illustrating a method of acquiring blood vessel information from a medical image, according to an exemplary embodiment.

Figure 5:
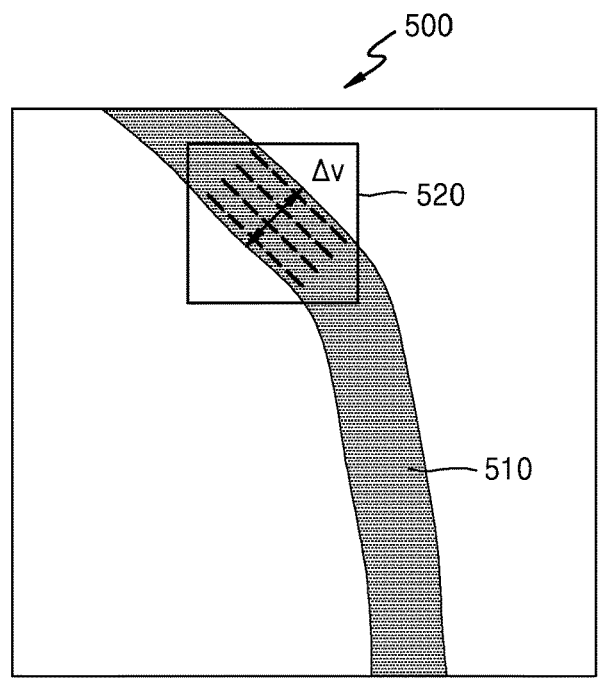
FIG. 5 is a conceptual diagram illustrating an ROI according to an exemplary embodiment.

A medical imaging apparatus, as illustrated in FIG. 5, may set a region of interest (ROI) including a blood vessel 510 in a medical image 500. In operation S310, the medical imaging apparatus may analyze blood vessel information that is information about the blood vessel 510 included in the ROI 520. The blood vessel information may include at least one from among a diameter of the blood vessel 510, a central point (or a center of the diameter) of the blood vessel 510, an angle of the blood vessel 510 with respect to a horizontal direction, and any bifurcation and/or crossover of the blood vessel 510 in the ROI 520. The medical imaging apparatus may determine a diameter $\Delta v$ of a blood vessel, based on a region which is detected as the blood vessel from a medical image. The medical imaging apparatus may measure the number of virtual rays $N_{VR}$ in consideration of the diameter $\Delta v$ of the blood vessel. Also, the medical imaging apparatus may determine a center of the diameter $\Delta v$ as a central point of the blood vessel. The medical imaging apparatus may determine the number of virtual rays, based on the following Equation (1):

$$N_{VR} \propto \Delta v / \lambda \quad (1)$$

where $\lambda$ denotes an interval between a plurality of virtual rays.

when the number of virtual rays is determined, an angle of the blood vessel may be determined based on the following Equation (2). The angle of the blood vessel denotes a direction in which the blood vessel is inclined with respect to a horizontal direction in an image.

$$E(\theta) = \Sigma_{i=1}^{N_{VR}}(L_{i\_AVE} + \kappa * L_{i\_SD}), (-180 \leq \theta \leq 180) \quad (2)$$

where $E(\theta)$ denotes a representative angle value of a plurality of virtual rays having an angle $\Theta$ which is inclined with respect to the horizontal direction. $N_{VR}$ denotes the number of the virtual rays having the angle $\Theta$. $L_{i\_AVE}$ denotes a mean value of pixel values on an i-th virtual straight ray having the angle $\Theta$. $L_{i\_SD}$ denotes a standard deviation of the pixel values on the i-th virtual straight ray having the angle $\theta$, which is inclined with respect to the horizontal direction. The above-described method of calculating a diameter, a central point, and an angle of a blood vessel is only an example, and the exemplary embodiments are not limited thereto.

Subsequently, the medical imaging apparatus may track the blood vessel. Tracking the blood vessel denotes acquiring blood vessel information along the blood vessel in the medical image. That is, in operation S320, the medical imaging apparatus may determine whether to move an ROI, based on the blood vessel information. In operation S330, the medical imaging apparatus may move a position of the ROI according to a result of the determination of operation S320. Subsequently, the medical imaging apparatus may repeat operation S310, based on the moved position of the ROI.

Figure 6:
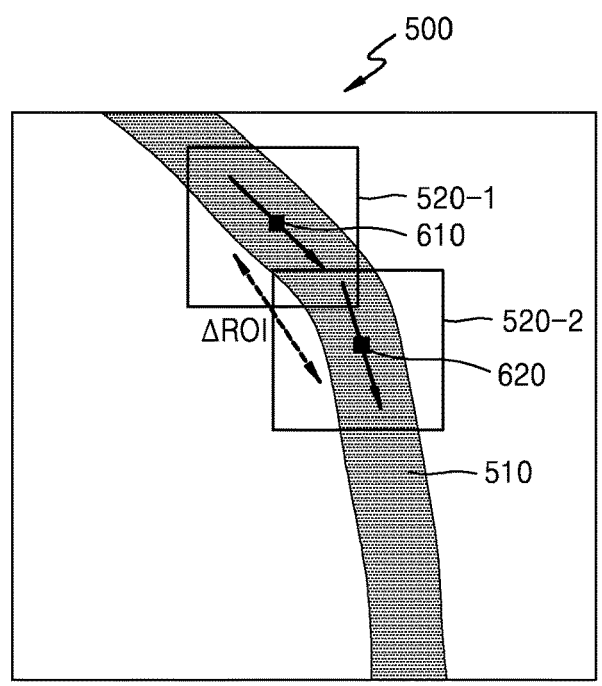
FIG. 6 is a conceptual diagram illustrating a method of moving a position of an ROI, according to an exemplary embodiment.

FIG. 6 is a conceptual diagram illustrating a method of moving a position of an ROI, according to an exemplary embodiment. Referring to FIG. 6, the medical imaging apparatus may acquire blood vessel information about a first ROI 520-1 which is set with respect to a first position 610 in a medical image 500. The medical imaging apparatus may determine a direction in which the ROI 520-1 is moved from the first position 610 according to an angle of the blood vessel 510. Also, the medical imaging apparatus may determine a distance $\Delta ROI$ by which the ROI is moved from the first position 610 according to a size of the first ROI 520-1. For example, the medical imaging apparatus may move the ROI, based on the following Equation (3):

$$\Delta ROI = k \times \Delta v \quad (3)$$

where $\Delta ROI$ denotes a movement distance of an ROI, and k denotes an arbitrary constant. For example, k may be determined within a range of 1 to 3. $\Delta v$ denotes a diameter of a blood vessel in the ROI.

Moreover, when bifurcation exists in the first ROI 520-1, the medical imaging apparatus may move the ROI in a plurality of directions. The medical imaging apparatus may acquire blood vessel information from a second ROI 520-2 which is set with respect to a second position 620. According to an exemplary embodiment, the medical imaging apparatus may set an area of the ROI to have a size that is proportional to a diameter of a blood vessel. For example, the medical imaging apparatus may determine a size of the ROI, based on the following Equation (4):

$$ROI_{size} \propto \alpha \times (\Delta v / \Delta \theta) \quad (4)$$

where $\Delta \theta$ denotes a difference between an angle, which is determined in an ROI that is analyzed in an immediately preceding stage, and an angle which is determined in an ROI that is analyzed in a next preceding stage. $\alpha$ denotes an arbitrary constant. $ROI_{size}$ denotes a size of the ROI.

When the medical imaging apparatus analyzes the blood vessel information at the first position 610, the medical imaging apparatus may acquire the blood vessel information from the second ROI 520-2 which is set at the second position 620, to which the ROI is moved, based on the first position 610 and the angle of the blood vessel 510.

Figure 4:
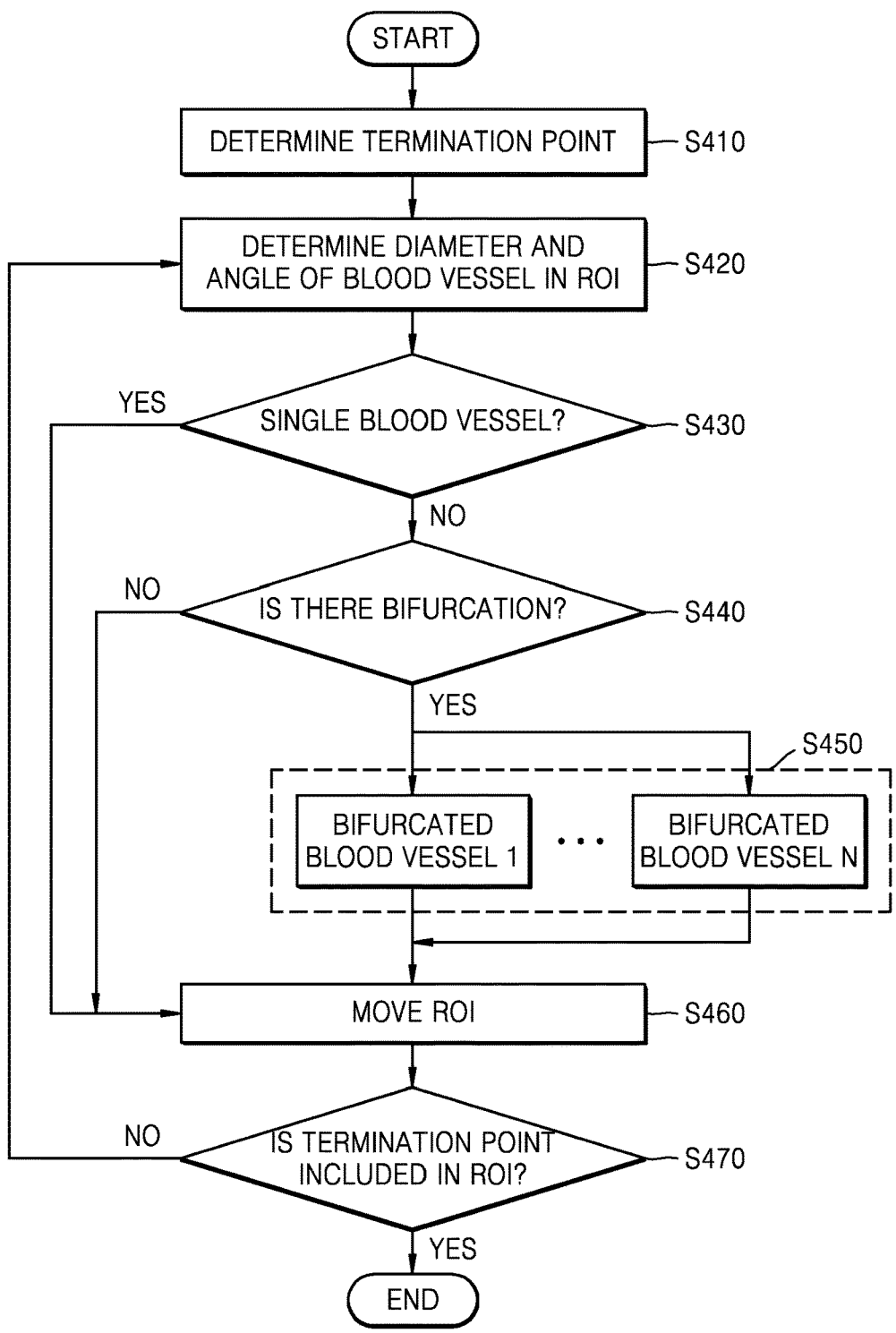
FIG. 4 is a flowchart illustrating a method of analyzing blood vessel information of a blood vessel included in a region of interest (ROI), according to an exemplary embodiment.

FIG. 4 is a flowchart illustrating a method of analyzing blood vessel information of a blood vessel included in an ROI, according to an exemplary embodiment.

First, in operation S410, a medical imaging apparatus may determine a termination point. The termination point may be set based on a user input, or the medical imaging apparatus may detect the termination point from a medical image.

Subsequently, in operation S420, the medical imaging apparatus may determine a diameter and an angle of a blood vessel included in an ROI. The medical imaging apparatus may determine the diameter $\Delta v$ of the blood vessel, based on a region which is detected as the blood vessel from the medical image. Also, the medical imaging apparatus may determine a central point of the blood vessel and the angle of the blood vessel by using a virtual ray illustrated in FIG. 5.

Subsequently, in operation S430, the medical imaging apparatus may determine whether a type of the blood vessel included in the ROI is a single blood vessel. The single blood vessel denotes a type of a blood vessel which does not meet another blood vessel. When a type of a blood vessel is a single blood vessel, as illustrated in FIG. 6, the medical imaging apparatus may move the ROI, based on the angle of the blood vessel in operation S460.

Figure 7:
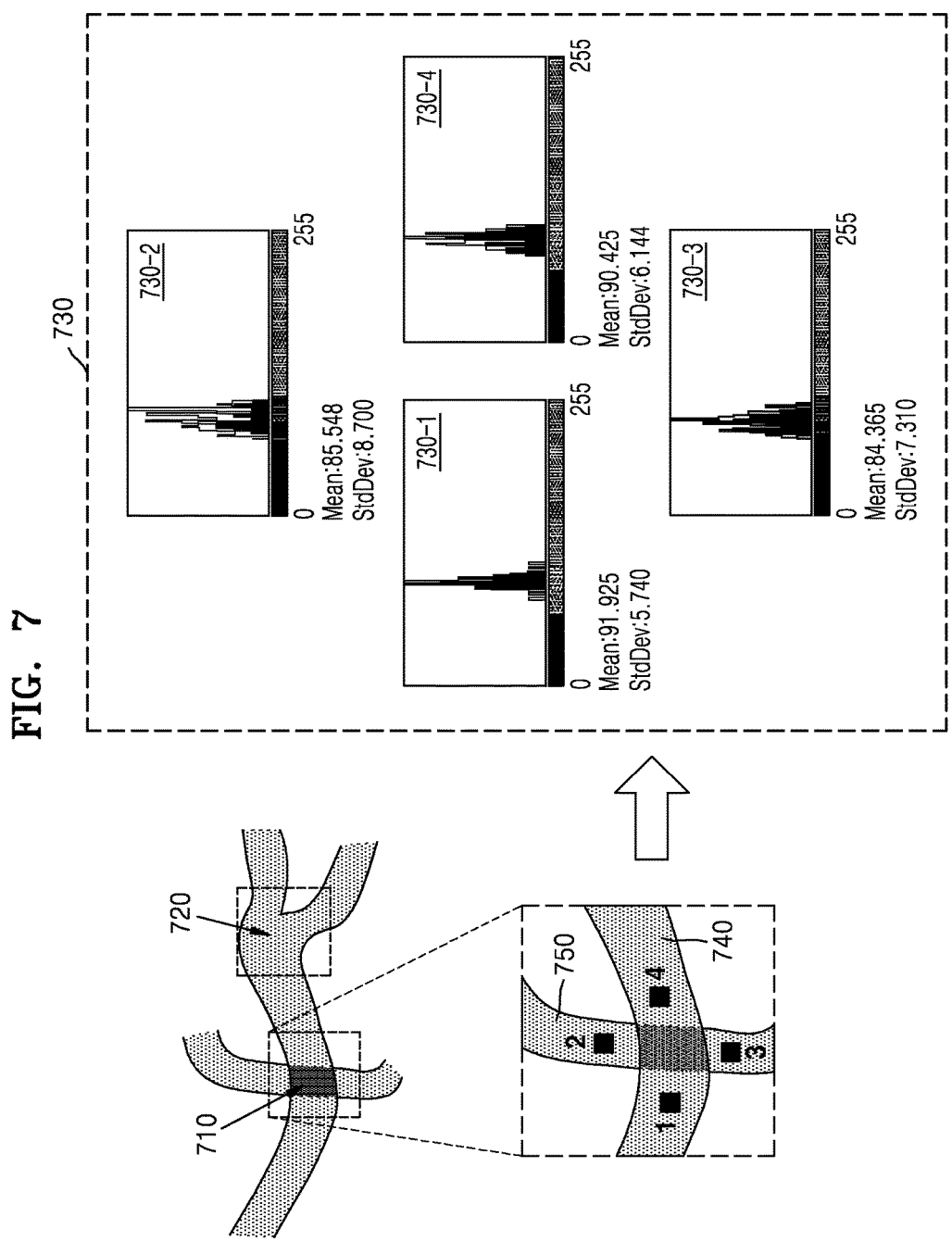
FIG. 7 is a conceptual diagram illustrating a method of detecting crossover and bifurcation, according to an exemplary embodiment.

Moreover, when there is a point in which a plurality of blood vessels meet each other in the ROI in operation S430, the medical imaging apparatus may determine whether the point in which the plurality of blood vessels meet each other is bifurcation or crossover in operation S440. FIG. 7 is a conceptual diagram illustrating a method of detecting crossover 710 and bifurcation 720, according to an exemplary embodiment. As illustrated in FIG. 7, there may be points 710 and 720 in which a plurality of blood vessels meet each other in an ROI. The medical imaging apparatus may detect bifurcation and/or crossover, based on pixel values 730 of a plurality of points 1, 2, 3, and 4 on a blood vessel near a point in which a plurality of blood vessels meet each other or a diameter of a blood vessel at the plurality of points 1-4.

For example, a diameter of a blood vessel 740 at a first point 1 may be similar to that at a fourth point 4, and a diameter of a blood vessel 730 at a second point 2 may be similar to that at a third point 3. Also, the diameter of the blood vessel 740 at the first point 1 may differ from the diameter of the blood vessel 750 at the second point 2. In this case, the medical imaging apparatus may determine that crossover is present in the blood vessel.

As another example, the medical imaging apparatus may compare the pixel values 730 of the plurality of points 1 to 4. As illustrated in FIG. 7, a mean pixel value (or a mean shadow) based on a spectrum 730-1 for the first point 1 and a mean pixel value (or a mean shadow) based on a spectrum 730-4 for the fourth point 4 are within a range of 90 to 92 and thus are similar. Also, a mean pixel value (or a mean shadow) based on a spectrum 730-2 for the second point 2 and a mean pixel value (or a mean shadow) based on a spectrum 730-3 for the third point 3 are within a range of 84 to 85 and thus are similar. In this case, the medical imaging apparatus may determine the point 710, in which the plurality of blood vessels meet each other, as crossover. On the other hand, when mean pixel values of the blood vessel at the respective points 1 to 4 are similar, the medical imaging apparatus may determine bifurcation is present in the blood vessel.

When a medical image is an angiography image, a contrast agent moves along with blood in a blood vessel. A range of a pixel value of a blood vessel that is shown in an angiography image is changed according to a concentration of a contrast agent in a blood vessel. Therefore, blood vessels that are bifurcated from a blood vessel may have mean pixel values of a similar range. On the other hand, blood vessels that cross each other may have mean pixel values of different ranges.

alternatively, detection of bifurcation by the medical imaging apparatus may be skipped, and whether bifurcation of a blood vessel exists in a medical image may be directly input by a user.

When it is determined that there is bifurcation in operation S440, the medical imaging apparatus may determine the number of bifurcated blood vessels, e.g., bifurcated blood vessel 1 to bifurcated blood vessel N, in operation S450. Here, the medical imaging apparatus may determine the number of bifurcated blood vessel, based on the number of bifurcations. For example, when there is one bifurcation, the medical imaging apparatus may determine the number of bifurcated blood vessels as two. Subsequently, in operation S460, the medical imaging apparatus may move the ROI in a plurality of directions, based on the number of bifurcated blood vessels. That is, when there are a plurality of bifurcated blood vessels, the medical imaging apparatus may track the bifurcated blood vessels.

Subsequently, in operation S470, the medical imaging apparatus may determine whether a termination point is included in an ROI which is set at a moved position. When the termination point is not included in the ROI, the medical imaging apparatus may again perform operation S420. When the termination point is included in the ROI, the medical imaging apparatus may terminate an analysis of a blood vessel.

Figure 8:
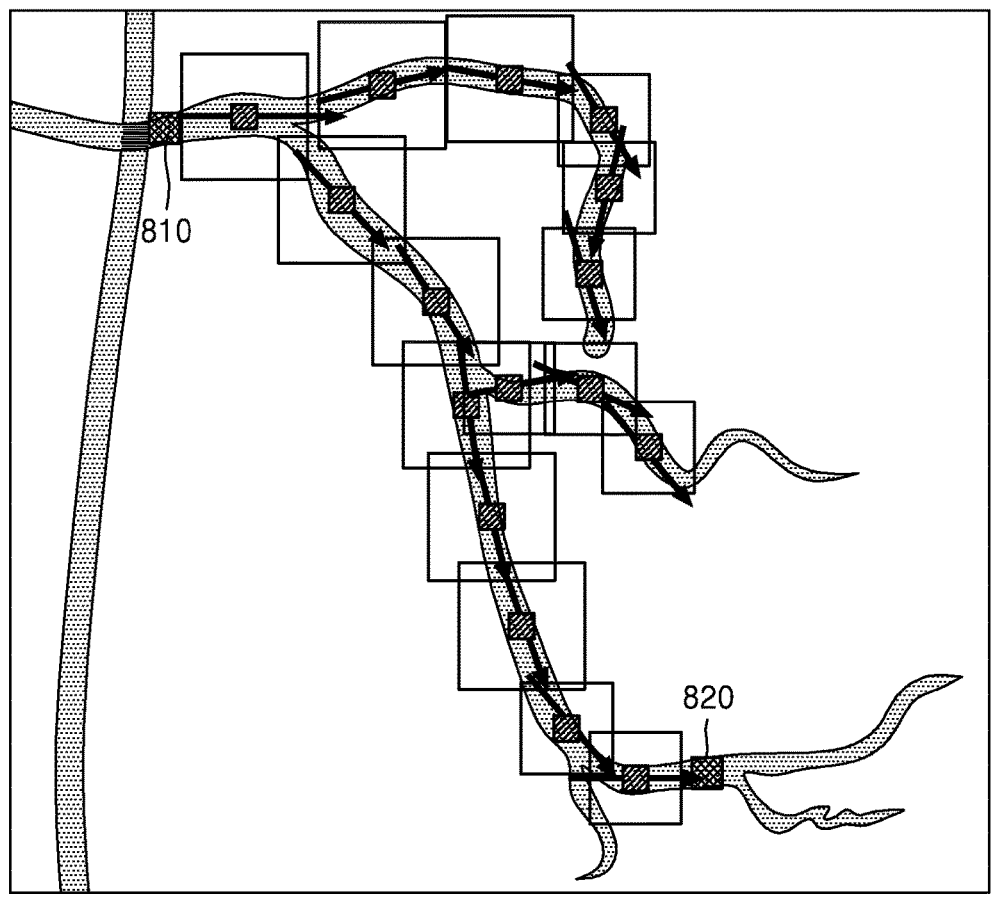
FIG. 8 is a conceptual diagram for describing a method of determining a traveling path, according to an exemplary embodiment.

FIG. 8 is a conceptual diagram for describing a method of determining a traveling path, according to an exemplary embodiment. According to an exemplary embodiment, the medical imaging apparatus may determine a start point 810 and a target point 820. The start point 810 and the target point 820 may be set by a user input. Alternatively, the medical imaging apparatus may determine a position, in which a catheter is inserted into a human body, as the start point 810 and determine a position of a lesion as the target point 820.

The medical imaging apparatus may search for all blood vessels from the start point 810 to the target point 820. When there is bifurcation, the medical imaging apparatus may determine a path for each of bifurcated blood vessels.

Figure 9:
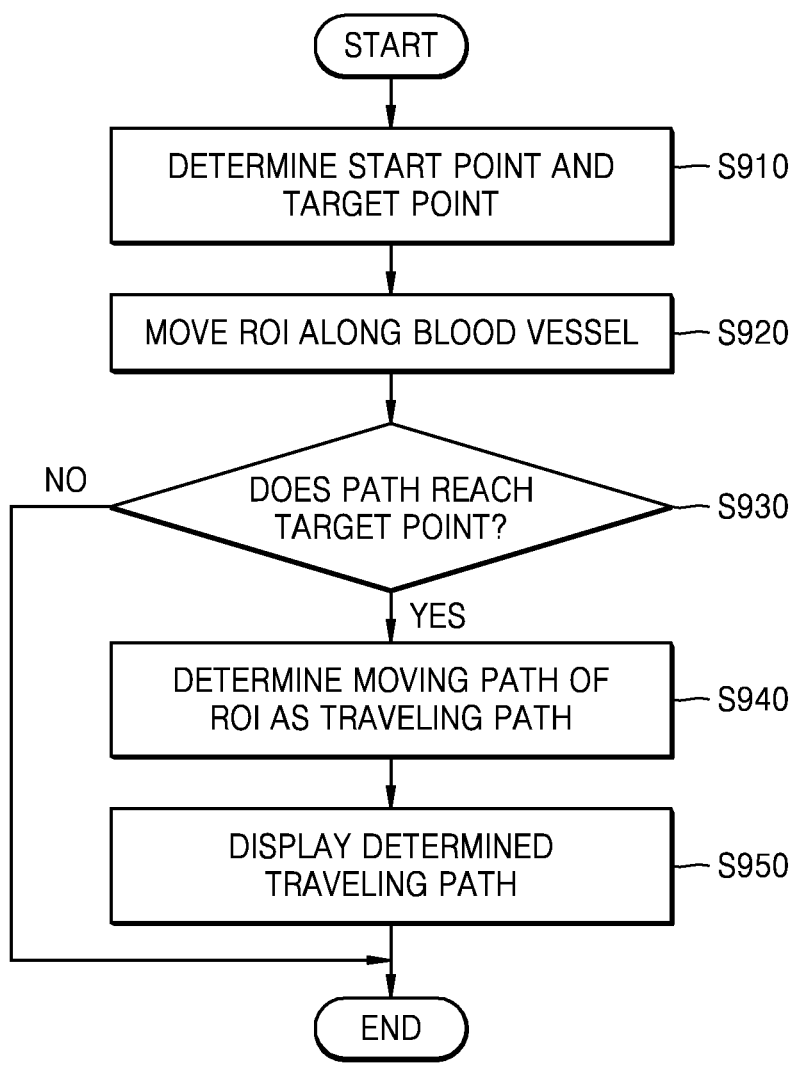
FIG. 9 is a flowchart illustrating a process of determining a traveling path, according to an exemplary embodiment.

FIG. 9 is a flowchart illustrating a process of determining a traveling path, according to an exemplary embodiment.

First, in operation S910, the medical imaging apparatus may determine a start point and a target point of a traveling path. Subsequently, in operation S920, the medical imaging apparatus may move an ROI along a blood vessel from the start point. In operation S920, the medical imaging apparatus may move the ROI, based on blood vessel information about a medical image.

The medical imaging apparatus may determine whether a target point is included in an ROI which moves along a blood vessel. When the target point is included in the moved ROI, the medical imaging apparatus may determine that the target point is reachable from the traveling path in operation S930. When it is determined that the target point is reachable from the traveling path, the medical imaging apparatus may determine the traveling path, based on a moving path of region of interest (ROI). The ROI may include information of interest (101), and the traveling path may be determined based on a moving path of the 101. For example, the medical imaging apparatus may determine a line, which is connected to a central point of a blood vessel included in the 101 which is moved, as the traveling path. Subsequently, in operation S950, the medical imaging apparatus may display the determined traveling path.

When it is determined that the target point is not reachable from the traveling path, the medical imaging apparatus may skip displaying a corresponding path.

Figure 10:
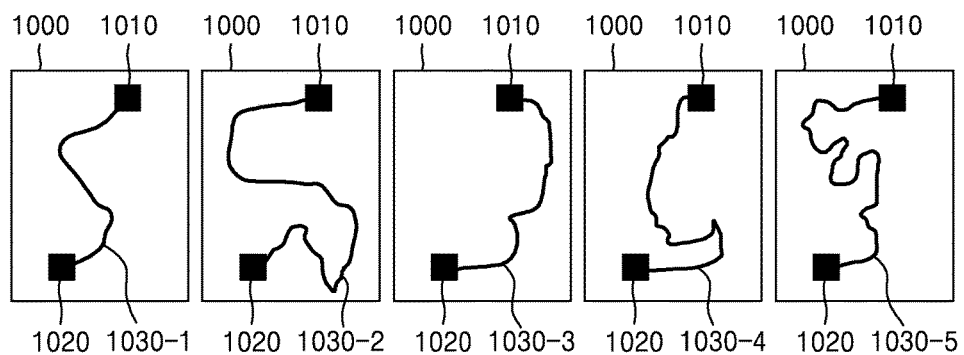
FIG. 10 is a conceptual diagram illustrating a plurality of displayed traveling paths according to an exemplary embodiment.

FIG. 10 is a conceptual diagram illustrating a plurality of displayed traveling paths according to an exemplary embodiment.

When bifurcation exists in a blood vessel, a medical imaging apparatus may determine a plurality of traveling paths 1030-1, 1030-2, 1030-3, 1030-4, and 1030-5 which lead from a start point 1010 to a target point 1020 in a medical image 1000. When there are the plurality of traveling paths 1030-1 to 1030-5 that lead from the start point 1010 to the target point 1020, the medical imaging apparatus may display the plurality of traveling paths 1030-1 to 1030-5. A user may select one traveling path from among the displayed plurality of traveling paths 1030-1 to 1030-5.

When one traveling path is selected, the medical imaging apparatus may display the selected traveling path along with a medical image.

Figure 11:
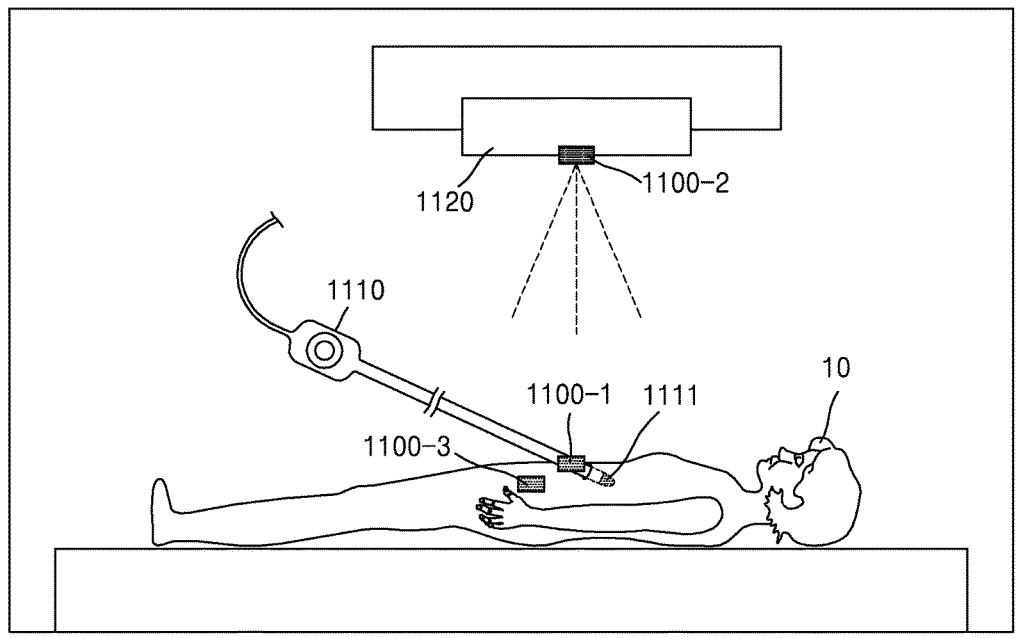
FIG. 11 is a conceptual diagram illustrating a position of a sensor according to an exemplary embodiment.
Figure 12:
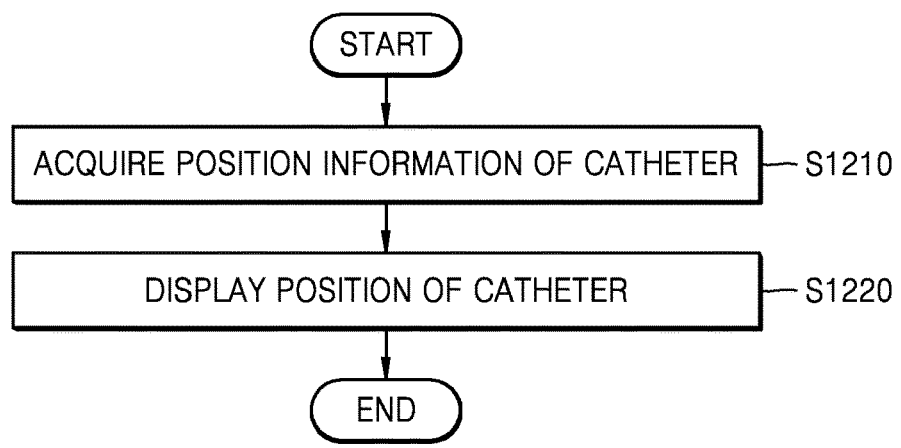
FIG. 12 is a flowchart illustrating a process of marking a position of a catheter on a medical image, according to an exemplary embodiment.

FIG. 11 is a conceptual diagram illustrating a position of a sensor according to an exemplary embodiment. FIG. 12 is a flowchart illustrating a process of marking a position of a catheter on a medical image, according to an exemplary embodiment.

A medical imaging apparatus according to an exemplary embodiment may acquire position information of a catheter 1110 by using a sensor. The position information of the catheter 1110 may indicate a position of a catheter tip 111 in a body 10 of a patient.

The medical imaging apparatus may acquire the position information of the catheter 1110 from first, second, and third sensors 1100-1, 1100-2, and 1100-3. According to an exemplary embodiment, the first sensor 1100-1 may be included in the catheter tip 1111. Also, the second and third sensors 1100-2, 1100-3 may be fixed to different positions. For example, the second sensor 1100-2 may be included in an angiography apparatus 1120, and the third sensor 1100-3 may be attached to an external point of the body 10 of the patient. The first, second, and third sensors 1100-1, 1100-2, and 1100-3 may sense a distance between the first, second, and third sensors 1100-1, 1100-2, and 1100-3.

When information on a distance between the sensors 1100-1, 1100-2, and 1100-3 is acquired from the three sensors 1100-1, 1100-2, and 1100-3, the medical imaging apparatus may acquire a position of the first sensor 1100-1 included in the catheter tip 1111 by using fixed positions of the second and third sensors 1100-2 and 1100-3.

The medical imaging apparatus may acquire a position of the catheter 1110 in operation S1210, and mark the acquired disposition of the catheter 1110 on a medical image. The position of the catheter 1110 may include a position of the catheter tip 1111.

Moreover, according to an exemplary embodiment, the medical imaging apparatus may match a 3D medical image with the 2D medical image. In a related art, it takes a long time to match medical images acquired from different types of imaging apparatuses. For example, it takes a long time to match an angiography image, which is a 2D image, with an MRA image, which is a 3D image. Therefore, in the related art, a medical image which is provided to a user in real time during a medical procedure is a 2D image. However, according to an exemplary embodiment, the 2D medical image is more easily matched with a 3D image by using position information of a catheter inserted in the body 10.

A path through which the catheter has moved indicates an actual state of a blood vessel. Thus, the path through which the catheter has moved may be used for matching a medical image with a blood vessel included in a 3D image. A path through which a catheter has moved in a medical image may correspond to a position corresponding to a 3D image by using position information of the catheter, and thus, the 2D medical image is more easily matched with a 3D medical image. After the 2D medical image is matched with the 3D image, the medical imaging apparatus may mark a position of the catheter on the 3D medical image. Also, the medical imaging apparatus may determine a traveling path, which is generated based on the 2D medical image, and a 3D traveling path corresponding to the position information of the catheter in the 3D medical image. The 3D traveling path denotes a path in which the traveling path generated based on the 2D medical image is marked on the 3D medical image.

That is, the medical imaging apparatus according to an exemplary embodiment may mark, on a 3D medical image matched with a 2D medical image, an insertion position of a catheter, a current position of the catheter, a path through which the catheter has passed, and a path through which the catheter is to pass to reach a target point.

Figure 13:
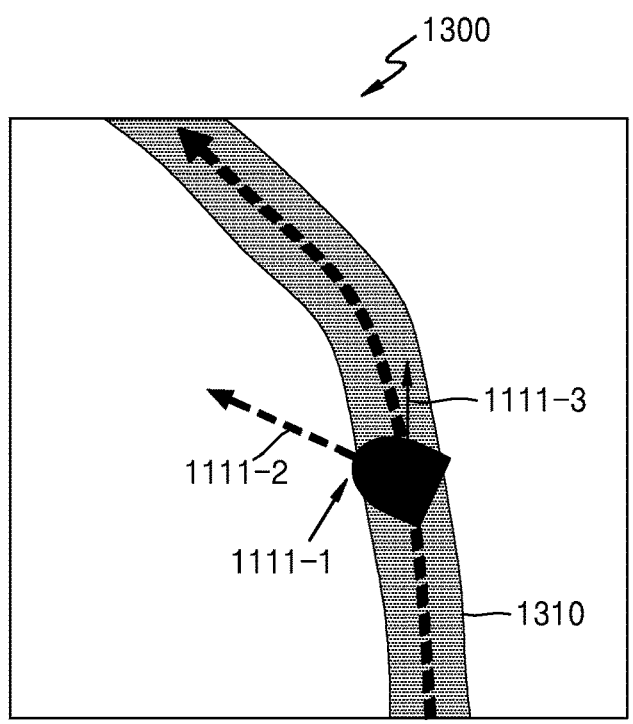
FIG. 13 is a conceptual diagram illustrating a position of a catheter marked on a medical image according to an exemplary embodiment.

FIG. 13 is a conceptual diagram illustrating a position 1111-1 of a catheter marked on a medical image 1300 according to an exemplary embodiment. A medical imaging apparatus may mark the position 1111-1 of the catheter on the medical image 1300, based on position information of the catheter. According to an exemplary embodiment, the medical imaging apparatus may generate and output feedback information, based on the position information of the catheter and blood vessel information. For example, when a traveling direction 1111-2 of the catheter differs from a direction 1111-3 of a blood vessel 1310, a wall of the blood vessel 1310 may be damaged by the catheter 1111-1. In this case, the medical imaging apparatus may output the feedback information.

the feedback information may be output as a physical force such as a pressure, a tension, a stress, or a vibration. For example, a catheter manipulator for manipulating a catheter may include a mechanical apparatus. When the feedback information is generated, the catheter manipulator may output the feedback information by applying a physical force to a user by using the mechanical apparatus. However, the exemplary embodiments are not limited thereto. The feedback information may be output by various different methods.

The medical imaging apparatus may output the feedback information in various cases. For example, when a catheter tip collides with a wall of a blood vessel or a friction occurs, the medical imaging apparatus may output the feedback information. As another example, when the position information of the catheter deviates from a traveling path displayed by the medical imaging apparatus, the medical imaging apparatus may output the feedback information. Alternatively, when a curvature of a wire configuring the catheter is equal to or greater than a threshold value, the medical imaging apparatus may output the feedback information. Alternatively, when the catheter moves from a bifurcation point to one of bifurcated blood vessels, the medical imaging apparatus may output the feedback information. Alternatively, when the catheter moves to a blood vessel of which a diameter is equal to or less than a threshold value, the medical imaging apparatus may output the feedback information.

According to an exemplary embodiment, the medical imaging apparatus may acquire traveling history information that indicates a history of positions to which the catheter has moved. The medical imaging apparatus may reconstruct blood vessel information or a medical image, based on the traveling history information of the catheter. As described above, a moving path of the catheter represents an actual state of a blood vessel. Therefore, when the traveling history information of the catheter does not match the blood vessel information or the medical image, the medical imaging apparatus may reconstruct the blood vessel information or the medical image, based on the traveling history information.

Figure 14:
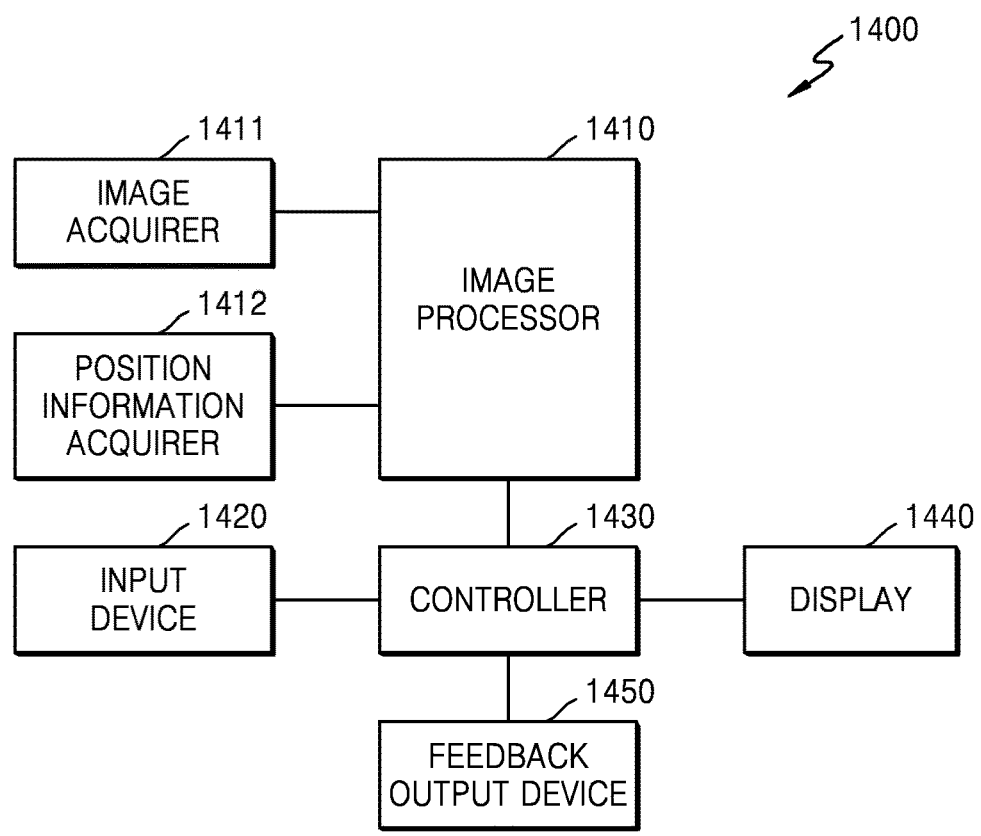
FIG. 14 is a block diagram illustrating a structure of a medical imaging apparatus according to an exemplary embodiment.
Figure 15:
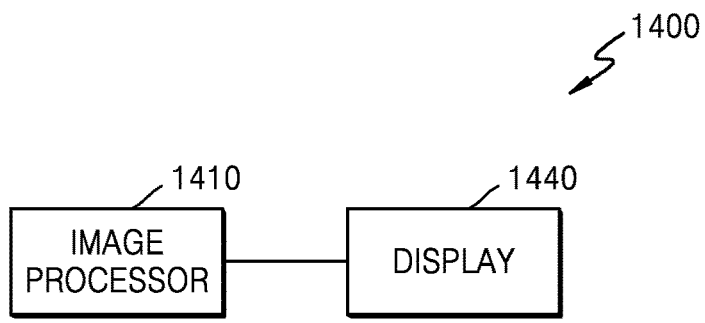
FIG. 15 is a block diagram illustrating a structure of a medical imaging apparatus according to an exemplary embodiment.

FIG. 14 is a block diagram illustrating a structure of a medical imaging apparatus 1400 according to an exemplary embodiment. The medical imaging apparatus 1400 according to an exemplary embodiment may include an image acquirer 1411, a position information acquirer 1412, an image processor 1410, a controller 1430, an input device 1420, a display 1440, and a feedback output device 1450. FIG. 15 is a block diagram illustrating a structure of a medical imaging apparatus according to another exemplary embodiment. The medical imaging apparatus 1400 according to another exemplary embodiment may include an image processor 1410 and a display 1440. FIGS. 14 and 15 are merely examples and the exemplary embodiments are not limited thereto. According to exemplary embodiments, the medical imaging apparatus 1400 may include more elements. Alternatively, the elements illustrated in FIGS. 14 and 15 may be replaced with similar elements.

The image acquirer 1411 may acquire a medical image. For example, the image acquirer 1411 may transmit X-rays to a body of a patient to acquire an angiography image.

the image processor 1410 may include at least one processor for processing an image. The image processor 1410 may acquire blood vessel information from a medical image acquired by the image processor 1411. According to an exemplary embodiment, the image processor 1410 may set an ROI, determine a diameter and an angle of a blood vessel included in the ROI, and detect bifurcation and/or crossover. Also, the image processor 1410 may acquire blood vessel information while tracking a blood vessel included in the medical image. That is, the image processor 1410 may acquire blood vessel information from a first ROI which is set at a first position, and acquire blood vessel information from a second ROI which is set at a second position which is moved from the first position based on the angle of the blood vessel. By repeating the above-described method, the image processor 1410 may acquire blood vessel information while tracking a blood vessel in the medical image.

The image processor 1410 may determine the diameter $\Delta v$ of the blood vessel, based on a region which is detected as the blood vessel from the medical image. The image processor 1410 may measure the number of virtual rays $N_{VR}$ in consideration of the diameter of the blood vessel. Also, the image processor 1410 may determine a center of the diameter as a central point of the blood vessel. The image processor 1410 may set a virtual ray in the blood vessel included in the ROI, and determine the angle of the blood vessel by using the virtual ray.

Moreover, when there is a point in which a plurality of blood vessels meet each other in the ROI, the image processor 1410 may determine whether the point in which the plurality of blood vessels meet each other is bifurcation or crossover. As described above with reference to FIG. 7, there may be the points 710 and 720 in which a plurality of blood vessels meet each other in an ROI. The medical imaging apparatus may detect bifurcation and/or crossover, based on the pixel values 730 of the plurality of points 1 to 4 on a blood vessel near a point in which a plurality of blood vessels meet each other or a diameter of a blood vessel at the plurality of points 1 to 4.

For example, as shown in FIG. 7, a diameter of the blood vessel at the first point 1 may be similar to that at the fourth point 4, and a diameter of the blood vessel at the second point 2 may be similar to that at the third point 3. Also, the diameter of the blood vessel at the first point 1 may differ from the blood vessel at the second point 2. In this case, the medical imaging apparatus may determine that crossover is present in the blood vessel.

As another example, the medical imaging apparatus may compare the pixel values 730 of the plurality of points 1 to 4. As illustrated in FIG. 7, a mean pixel value (or a mean shadow) based on the spectrum 730-1 for the first point 1 and a mean pixel value (or a mean shadow) based on the spectrum 730-4 for the fourth point 4 are within a range of 90 to 92 and thus are similar. Also, a mean pixel value (or a mean shadow) based on the spectrum 730-2 for the second point 2 and a mean pixel value (or a mean shadow) based on the spectrum 730-3 for the third point 3 are within a range of 84 to 85 and thus are similar. In this case, the medical imaging apparatus may determine the point 710, in which the plurality of blood vessels meet each other, as crossover. On the other hand, when mean pixel values of the blood vessel at the respective points 1 to 4 are similar, the medical imaging apparatus may determine that bifurcation is present in the blood vessel. When a medical image is an angiography image, a contrast agent moves along with blood in a blood vessel.

A range of a pixel value of a blood vessel that is shown in an angiography image is changed according to a concentration of a contrast agent in a blood vessel. Therefore, blood vessels that are bifurcated from a blood vessel may have mean pixel values of a similar range. On the other hand, blood vessels that cross each other may have mean pixel values of different ranges.

Alternatively, detection of bifurcation by the medical imaging apparatus may be skipped, and whether bifurcation of a blood vessel exists in a medical image may be directly input by a user.

Moreover, the image processor 1410 may determine a traveling path, based on a start point, a target point, and blood vessel information. The start point and the target point may be input by a user through the input device 1420, or the image processor 1410 may detect the start point and the target point from the medical image. The image processor 1410 may search for all blood vessels from the start point to the target point. When there is bifurcation, the image processor 1410 may determine a path for each of bifurcated blood vessels.

The position information acquirer 1412 may acquire position information of a catheter by using a sensor. For example, as illustrated in FIG. 11, the position information acquirer 1412 may acquire the position information of the catheter by using a position sensor included in the catheter and two fixed position sensors. The position information of the catheter may indicate a position of a catheter tip in a body of a patient. Also, the position information acquirer 1412 may acquire traveling history information indicating a path through which the catheter has moved, based on the position information of the catheter.

The image processor 1410 may match a 2D medical image with a 3D medical image. Here, the image processor 1410 may match the 2D medical image with the 3D medical image by using traveling history information acquired by the position information acquirer 1412. A path through which the catheter has moved indicates an actual state of a blood vessel. Thus, the path through which the catheter has moved may be used for matching the medical image with a blood vessel included in the 3D medical image. A path through which a catheter has moved in the medical image may correspond to a position corresponding to the 3D medical image by using position information of the catheter, and thus, the 2D medical image is more easily matched with the 3D medical image. Also, the image processor 1410 may determine a 3D traveling path for marking a traveling path, which is determined based on the 2D medical image, on the 3D medical image.

The input device 1420 denotes an apparatus which is used for a user to control the medical imaging apparatus 1400 or input information to the medical imaging apparatus 1400. The input device 1420 may include a trackball, a keypad, or a touch screen, but is not limited thereto.

The display 1440 according to an exemplary embodiment denotes an apparatus for outputting an image. The display 1440 may include a liquid crystal display (LCD), a plasma display panel (PDP), a transparent display, a flexible display, or a cathode ray tube (CRT) display, but is not limited thereto. The display 1440 may display the medical image acquired by the image acquirer 1411. Here, the display 1440 may display blood vessel information acquired by the image processor 1410 along with the medical image.

Moreover, when a traveling path is determined by the image processor 1410, the display 1440 may display the determined traveling path along with the medical image. When a 3D traveling path is determined by the image processor 1410, the display 1440 may display the determined 3D traveling path along with the 3D medical image. Also, the display 1440 may further display a position of the catheter included in the 3D medical image, based on the position information of the catheter acquired by the position information acquirer 1412. Referring again to FIG. 13, the position 1111-1 of the catheter may be marked on the medical image 1300 according to an exemplary embodiment.

The image processor 1410 may generate the feedback information, based on the position information of the catheter and the blood vessel information. The feedback output device 1450 may output the generated feedback information. The feedback output device 1450 may output the feedback information in various methods by using, for example, a physical force, a vibration, a sound, or a light source. For example, referring again to FIG. 13, when the traveling direction 1111-2 of the catheter differs from the direction 1111-3 of the blood vessel 1310, the wall of the blood vessel may be damaged by the catheter 1111-1. In this case, the feedback output device 1450 may generate the feedback information in the form of, for example, a vibration in the catheter or generate an alarm sound. According to an exemplary embodiment, the feedback output device 1450 may include a mechanical apparatus for generating a physical force such as a pressure, a tension, or a stress.

The image processor 1410 may output the feedback information in various cases. For example, when a catheter tip collides with a wall of a blood vessel or friction occurs, the image processor 1410 may output the feedback information. As another example, when the position information of the catheter deviates from a traveling path displayed by the medical imaging apparatus, the image processor 1410 may output the feedback information. Alternatively, when a curvature of a wire configuring the catheter is equal to or greater than a threshold value, the image processor 1410 may output the feedback information. Alternatively, when the catheter moves from a bifurcation point to one of bifurcated blood vessels, the image processor 1410 may output the feedback information. Alternatively, when the catheter moves to a blood vessel of which a diameter is equal to or less than a threshold value, the image processor 1410 may output the feedback information.

The controller 1430 may control an overall operation of the medical imaging apparatus 1400. For example, the controller 1400 may be a processor. Some or all of the image acquirer 1411, the position information acquirer 1412, the image processor 1410, the controller 1430, the input device 1420, the display 1440, and the feedback output device 1450 may be operated by a software element, but are not limited thereto. Some of the above-described elements may be operated by a hardware element. Also, at least some of the image acquirer 1411, the position information acquirer 1412, and the image processor 1410 may be included in the controller 1430, but are not limited to.

As described above, according to the one or more of the above exemplary embodiments, accurate information of a blood vessel may be acquired from a medical image including a blood vessel.

Moreover, according to the exemplary embodiments, by providing a traveling path of a catheter to an operator, it is possible for the operator to more easily determine a procedure plan.

Moreover, according to the exemplary embodiments, a position of an inserted catheter is more accurately marked on a medical image.

Moreover, according to the exemplary embodiments, an operator easily performs a blood vessel intervention by using a 3D image.

Moreover, according to the exemplary embodiments, by providing a feedback to a user, a wall of a blood vessel is prevented from being damaged by an excessive or erroneous movement of a catheter.

Moreover, according to the exemplary embodiments, an amount of radiation exposed to a patient is reduced, and an operator of which a skill level is low performs a blood vessel intervention more easily.

The exemplary embodiment of the inventive concept may be implemented in the form of a storage medium that includes computer executable instructions, such as program modules, being executed by a computer. Computer-readable media may be any available media that may be accessed by the computer and includes volatile media such as a random access memory (RAM), nonvolatile media such as a read only memory (ROM), and removable and non-removable media. In addition, the computer-readable media may include computer storage media and communication media. Computer storage media includes the volatile media, non-volatile media, and removable and non-removable media implemented as any method or technology for storage of information such as computer readable instructions, data structures, program modules, or other data. The medium of communication is typically computer-readable instructions, and other data in a modulated data signal such as data structures, or program modules, or other transport mechanism and includes any information delivery media. Examples of the computer storage media include, for example, ROM, RAM, a flash memory, a compact disc (CD), a digital versatile disc (DVD), a magnetic disc, or a magnetic tape.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of providing a medical image by using a medical imaging apparatus, the method comprising:
   determining a start point and a target point in the medical image;
   acquiring blood vessel information comprising a diameter and an angle of a blood vessel, which is included in the medical image, from the start point; and
   displaying the medical image and a traveling path from the start point to the target point based on the blood vessel information, wherein
the acquiring of the blood vessel information comprises:
acquiring first blood vessel information of the blood vessel in a region of interest (ROI) with respect to a first position in the medical image;
if there is a point in which a plurality of blood vessels including the blood vessel meet each other in the ROI with respect to the first position, determining whether the point is a bifurcation point or a crossover point based on pixel values of a plurality of points near the point or diameters of the plurality of blood vessels at the plurality of points;
if the point is the bifurcation point, moving a position of the ROI in each direction along bifurcated blood vessels according to the first blood vessel information;
if the point is the crossover point, moving a position of the ROI in a direction along the blood vessel according to the first blood vessel information;
acquiring second blood vessel information of the blood vessel in the ROI with respect to a second position which is moved from the first position; and
determining the traveling path based on a moving path of the ROI.

2. The method of claim 1, wherein the
first blood vessel information comprises a first diameter of the blood vessel and a first angle of the blood vessel in the ROI with respect to the first position and the second blood vessel information comprises a second diameter of the blood vessel and a second angle of the blood vessel in the ROI with respect to the second position.

3. The method of claim 1, wherein the displaying the medical image and the traveling path comprises displaying a plurality of traveling paths including the traveling path according to a number of bifurcation points based on the blood vessel information.

4. The method of claim 1, wherein the medical image is a two-dimensional (2D) medical image, and the method further comprises:
matching the 2D medical image with a three-dimensional (3D) medical image; and
determining a 3D traveling path corresponding to the traveling path in the 2D medical image,
wherein the displaying the medical image and the traveling path comprises displaying the 3D medical image including the 3D traveling path.

5. The method of claim 1, further comprising:
acquiring position information of a catheter by using a first position sensor included in the catheter and a second position sensor disposed at a fixed location,
wherein the displaying the medical image and the traveling path comprises displaying a position of the catheter on the medical image, based on the position information.

6. The method of claim 5, further comprising:
outputting feedback information, based on the position information of the catheter and the blood vessel information.

7. The method of claim 5, further comprising:
acquiring traveling history information indicating a history of the position information of the catheter according to movement of the catheter; and
updating at least one among the medical image and the blood vessel information, based on the traveling history information.

8. A medical imaging apparatus for providing a medical image, the medical imaging apparatus comprising:
an image processor configured to determine a start point and a target point in the medical image and acquire blood vessel information comprising a diameter and an angle of a blood vessel, which is included in the medical image, from the start point; and
a display configured to display the medical image and a traveling path from the start point to the target point based on the blood vessel information,
wherein
the image processor is further configured to:
acquire first blood vessel information of the blood vessel in a region of interest (ROI) with respect to a first position in the medical image;
if there is a point in which a plurality of blood vessels including the blood vessel meet each other in the ROI with respect to the first position, determine whether the point is a bifurcation point or a crossover point based on pixel values of a plurality of points near the point or diameters of the plurality of blood vessels at the plurality of points;
if the point is the bifurcation point, move a position of the ROI in each direction along bifurcated blood vessels according to the first blood vessel information;
if the point is the crossover point, move a position of the ROI in a direction along the blood vessel according to the first blood vessel information;
acquire second blood vessel information of the blood vessel in the ROI with respect to a second position which is moved from the first position, and
determine the traveling path based on a moving path of the ROI.

9. The medical imaging apparatus of claim 8, wherein the first blood vessel information comprises a first diameter of the blood vessel and a first angle of the blood vessel in the ROI with respect to the first position and the second blood vessel information comprises a second diameter of the blood vessel and a second angle of the blood vessel in the ROI with respect to the second position.

10. The medical imaging apparatus of claim 8, further comprising:
an input device configured to receive an input from a user,
wherein the image processor is further configured to determine the start point and the target point in the medical image, based on the received input.

11. The medical imaging apparatus of claim 8, wherein the display is further configured to display a plurality of traveling paths including the traveling path according to a number of bifurcation points based on the blood vessel information.

12. The medical imaging apparatus of claim 11, wherein the medical image is a two-dimensional (2D) medical image,
the image processor is further configured to match the 2D medical image with a three-dimensional (3D) medical image, and configured to determine a 3D traveling path corresponding to the traveling path of the 2D medical image, and
the display is further configured to display the 3D medical image including the 3D traveling path.

13. The medical imaging apparatus of claim 8, further comprising:
a position information acquirer configured to acquire position information of a catheter by using a first position sensor included in the catheter and a second position sensor disposed at a fixed location, wherein the display is further configured to display a position of the catheter on the medical image, based on the position information.

14. The medical imaging apparatus of claim 13, further comprising:
a feedback output device configured to output feedback information, based on the position information of the catheter and the blood vessel information.

15. The medical imaging apparatus of claim 13, wherein the image processor is further configured to acquire traveling history information indicating a history of the position information of the catheter according to movement of the catheter, and update at least one among the medical image and the blood vessel information, based on the traveling history information.

16. A non-transitory computer-readable storage medium storing a program for executing the method of claim 1.

17. The medical imaging apparatus of claim 9, wherein the image processor is further configured to set the ROI with respect to the second position, and
a size of the ROI with respect to the second position is determined by using the following equation:

$$ROIsize = \alpha \times (\Delta v / \Delta \theta),$$

wherein $\alpha$ denotes a constant, $\Delta v$ denotes the first diameter of the blood vessel, and $\Delta \theta$ denotes a difference between the first angle of the blood vessel and an angle of the blood vessel in the ROI with respect a position preceding the first position.

18. The medical imaging apparatus of claim 14, wherein the feedback output device is further configured to output the feedback information, when the position information of the catheter deviates from the traveling path.

* * * * *